US012727761B2

(12) United States Patent
Peterson et al.

(10) Patent No.: US 12,727,761 B2
(45) Date of Patent: Sep. 8, 2026

(54) DOSIMETRY SYSTEM FOR PHOTODYNAMIC ANITMICROBIAL THERAPY DEVICE OF INFECTIOUS KERATITIS

(71) Applicant: UNIVERSITY OF MIAMI, Miami, FL (US)

(72) Inventors: Jeffrey Carl Peterson, Miami, FL (US); Jean-Marie Parel, Miami, FL (US); Fabrice Manns, Miami, FL (US); Marco Ruggeri, Miami, FL (US)

(73) Assignee: University of Miami, Miami, FL (US)

( * ) Notice: Subject to any disclaimer, the term of this patent is extended or adjusted under 35 U.S.C. 154(b) by 966 days.

(21) Appl. No.: 17/925,969

(22) PCT Filed: May 21, 2021

(86) PCT No.: PCT/US2021/033729
§ 371 (c)(1),
(2) Date: Nov. 17, 2022

(87) PCT Pub. No.: WO2021/237131
PCT Pub. Date: Nov. 25, 2021

(65) Prior Publication Data

US 2023/0194734 A1 Jun. 22, 2023

Related U.S. Application Data

(60) Provisional application No. 63/040,634, filed on Jun. 18, 2020, provisional application No. 63/028,328, filed on May 21, 2020.

(51) Int. Cl.
*A61B 5/00* (2006.01)
*A61B 5/1455* (2006.01)
(Continued)

(52) U.S. Cl.
CPC ........ *A61B 5/0071* (2013.01); *A61B 5/14551* (2013.01); *A61K 41/0057* (2013.01);
(Continued)

(58) Field of Classification Search
CPC .... A61K 41/0057; G01T 1/10; A61B 5/0071; A61B 5/062; A61B 5/4836; A61N 2005/0628
See application file for complete search history.

(56) References Cited

U.S. PATENT DOCUMENTS 8,304,746 B2 11/2012 Oda et al.
9,480,405 B2 * 11/2016 Oki .................... G01N 21/6456
(Continued)

FOREIGN PATENT DOCUMENTS

| | | | | |
|---|---|---|---|---|
| DE | 102008020755 A1 * | 10/2009 | ............. | C09B 69/10 |
| WO | WO-2007111408 A1 * | 10/2007 | ............. | A61N 5/062 |
| WO | 2020097186 A1 | 5/2020 | | |

OTHER PUBLICATIONS

Moritz, Tobias J. et al. "Multispectral singlet oxygen and photosensitizer luminescence dosimeter for continuous photodynamic therapy dose assessment during treatment". Journal of Biomedical Optics, 25(6), 063810, Mar. 13, 2020. (Year: 2020).*
(Continued)

*Primary Examiner* — Michael A Lyons
(74) *Attorney, Agent, or Firm* — Procopio, Cory, Hargreaves & Savitch LLP

(57) ABSTRACT

Systems and methods for an improved dosimeter for measuring dosage for photodynamic therapy treatment are provided. An example systems includes a dosimeter comprising a variable optical filter system configured to receive a second light, the second light comprising luminescence produced by singlet oxygen and one or more background signal and selectively transmit the luminescence and the one
(Continued)

or more background signals as a third light, the variable optical filter system comprises a plurality of optical band-pass filters that are switchable to selectively transmit the luminescence and the one or more background signals. The dosimeter also includes a photoreceiver configured to receive the third light and configured to generate electrical output signals corresponding to the luminescence and the one or more background signals, the electrical output signals being indicative of an amount of the singlet oxygen produced based on activating the photosensitizer.

21 Claims, 4 Drawing Sheets

(51) Int. Cl.

| | |
|---|---|
| ***A61K 41/00*** | (2020.01) |
| ***A61N 5/06*** | (2006.01) |
| ***G01T 1/10*** | (2006.01) |
| *G02B 5/20* | (2006.01) |
| *G02B 27/14* | (2006.01) |

(52) U.S. Cl.
CPC ................ *A61N 5/062* (2013.01); *G01T 1/10* (2013.01); *A61B 5/4836* (2013.01); *A61N 2005/0628* (2013.01); *G02B 5/20* (2013.01); *G02B 27/141* (2013.01)

(56) References Cited

U.S. PATENT DOCUMENTS

| | | | | |
|---|---|---|---|---|
| 2007/0060804 | A1* | 3/2007 | Thompson | A61B 5/0071 607/1 |
| 2010/0331927 | A1 | 12/2010 | Cottrell et al. | |
| 2012/0209125 | A1 | 8/2012 | Davis et al. | |
| 2014/0128799 | A1 | 5/2014 | Tanaka et al. | |
| 2019/0033486 | A1* | 1/2019 | Waslowski | G01V 8/12 |
| 2022/0001193 | A1* | 1/2022 | Zhu | G01N 21/64 |
| 2022/0062461 | A1* | 3/2022 | Chen | A61L 2/26 |
| 2022/0079446 | A1* | 3/2022 | König | A61B 5/0071 |

OTHER PUBLICATIONS

International Search Report and Written Opinion dated Sep. 14, 2021 in International Patent Application No. PCT/US2021/033729.

* cited by examiner

DOSIMETRY SYSTEM FOR PHOTODYNAMIC ANITMICROBIAL THERAPY DEVICE OF INFECTIOUS KERATITIS

CROSS-REFERENCE TO RELATED APPLICATIONS

This application claims priority under 35 U. S. C. § 119(e) to U.S. Provisional Patent App. No. 63/040,634, filed on Jun. 18, 2020 which is hereby incorporated herein by reference as if set forth in full. This application also claims priority under 35 U. S. C. § 119 (e) to U.S. Provisional Patent App. No. 63/028,328, filed on May 21, 2020, which is hereby incorporated herein by reference as if set forth in full.

BACKGROUND

Field of the Invention

The embodiments described herein are generally directed to ocular therapy, such as infectious keratitis, and, more particularly, to dosimeters and dosimetry systems for use in various ocular therapy applications.

Description of the Related Art

Corneal infection (such as infectious keratitis) is a common ocular emergency affecting ~25,000 Americans annually. It can lead to permanent damage to the cornea within a few days, and even possible blindness and complete loss of the eye if treatment fails. Approximately 10% of these infections result in the loss of two or more lines of visual acuity. There are various antimicrobial drugs to fight these infections, but they often have limited success against resistant or atypical organisms. This problem has compounded in recent years as more organisms become resistant to available antimicrobial drugs. When antimicrobial drugs fail, the cornea may continue to erode, necessitating an emergency corneal transplant (therapeutic penetrating keratoplasty or TPK). Due to ongoing active infection and inflammation, TPK has a 51% failure rate over a 5-year period. Because of this high failure rate and increasing rate of resistant keratitis infections, more options for effective therapies are needed.

Photodynamic therapy (PDT), which involves the use of light to excite a photosensitizing chemical substance (referred to as a photosensitizer), which produces singlet oxygen and or free radicals to elicit cell death (phototoxicity), can be used for the treatment of various ocular conditions, such as corneal and scleral infections such as infectious keratitis, keratoconus age-related macular degeneration, ocular squamous neoplasia (OSSN) or ocular surface malignancies (ophthalmologists), and outside of the eye has been used for treatment of skin, bladder, esophageal, breast, lung, gastrointestinal, prostate, and head and neck cancers, for autoimmune diseases such as psoriasis, as well as in skin infections and blood plasma sterilization. One such example of a clinical application of PDT is called by the ophthalmic community corneal crosslinking (CXL). This therapy works by applying drops of a photosensitizer, riboflavin, to the cornea stroma after removing the corneal epithelium and then activating the riboflavin with UV light. This is currently used as the standard of care for patients with progressive keratoconus and other forms of corneal ectasia.

PDT may be both minimally invasive and minimally toxic. Other light-based and laser therapies such as laser wound healing and rejuvenation, or intense pulsed light hair removal do not require a photosensitizer. PDT provides advantages that lessen the need for delicate surgery and lengthy recuperation and minimal formation of scar tissue and disfigurement. Some forms of PDT apply the photosensitizer systemically, which can cause a side effect is the associated photosensitization of skin tissue. The main limitation of PDT therapy is that light, photosensitizer, and in most cases oxygen, need to reach the tissue of interest in order to have an effect. Thus, if the tissue of interest is too deep to be reached by sufficient light or photosensitizer, or if oxygen depletion is a factor for that tissue, then the therapy may have limited efficacy.

To date there remains a need for improved PDT systems and therapeutic protocols that effectively treat diseases, minimize number of treatments, and minimize harmful effects.

SUMMARY

Accordingly, embodiments of an improved dosimetry system for use in various ocular therapy applications are disclosed. The following summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned herein.

In an embodiment, a dosimeter for photodynamic therapy is disclosed. The dosimeter comprises a variable optical filter system that is configured to receive a second light, the second light comprising luminescence produced by singlet oxygen and one or more background signals, each of which are based on irradiating a sample with a first light comprising a first wavelength within an excitation range of a photosensitizer applied to the sample, wherein activating the photosensitizer produces the singlet oxygen, and selectively transmit the luminescence and the one or more background signals as a third light, the variable optical filter system comprising a plurality of optical bandpass filters that are switchable to selectively transmit the luminescence and the one or more background signals. The dosimeter also comprises a photoreceiver configured to receive the third light and configured to generate electrical output signals corresponding to the luminescence and the one or more background signals, the electrical output signals being indicative of an amount of the singlet oxygen produced based on activating the photosensitizer.

In an embodiment, a dosimetry system is disclosed. The dosimeter system comprises the dosimeter as described above and a controller communicatively coupled to the photoreceiver and configured to receive the electrical output signals from the photoreceiver and generate a dosage measurement indicative of the amount of oxygen radicals produced based on activating the photosensitizer.

In an embodiment, a method for measuring dosage for photodynamic therapy treatment is disclosed. The method comprises deploying the dosimeter system as described above; iteratively selecting each optical bandpass filter of the plurality of optical bandpass filters to selectively filter the second light; for each optical bandpass filter, measuring, by the photoreceiver, an optical signal of the filtered second light and outputting the electrical output signal corresponding to the respective optical bandpass filter to the controller; and determining an amount of singlet oxygen produced by activating the photosensitizer by the light source based on the electrical output signals.

BRIEF DESCRIPTION OF THE DRAWINGS

The details of the present invention, both as to its structure and operation, may be gleaned in part by study of the accompanying drawings, in which like reference numerals refer to like parts, and in which.

Figure 1:
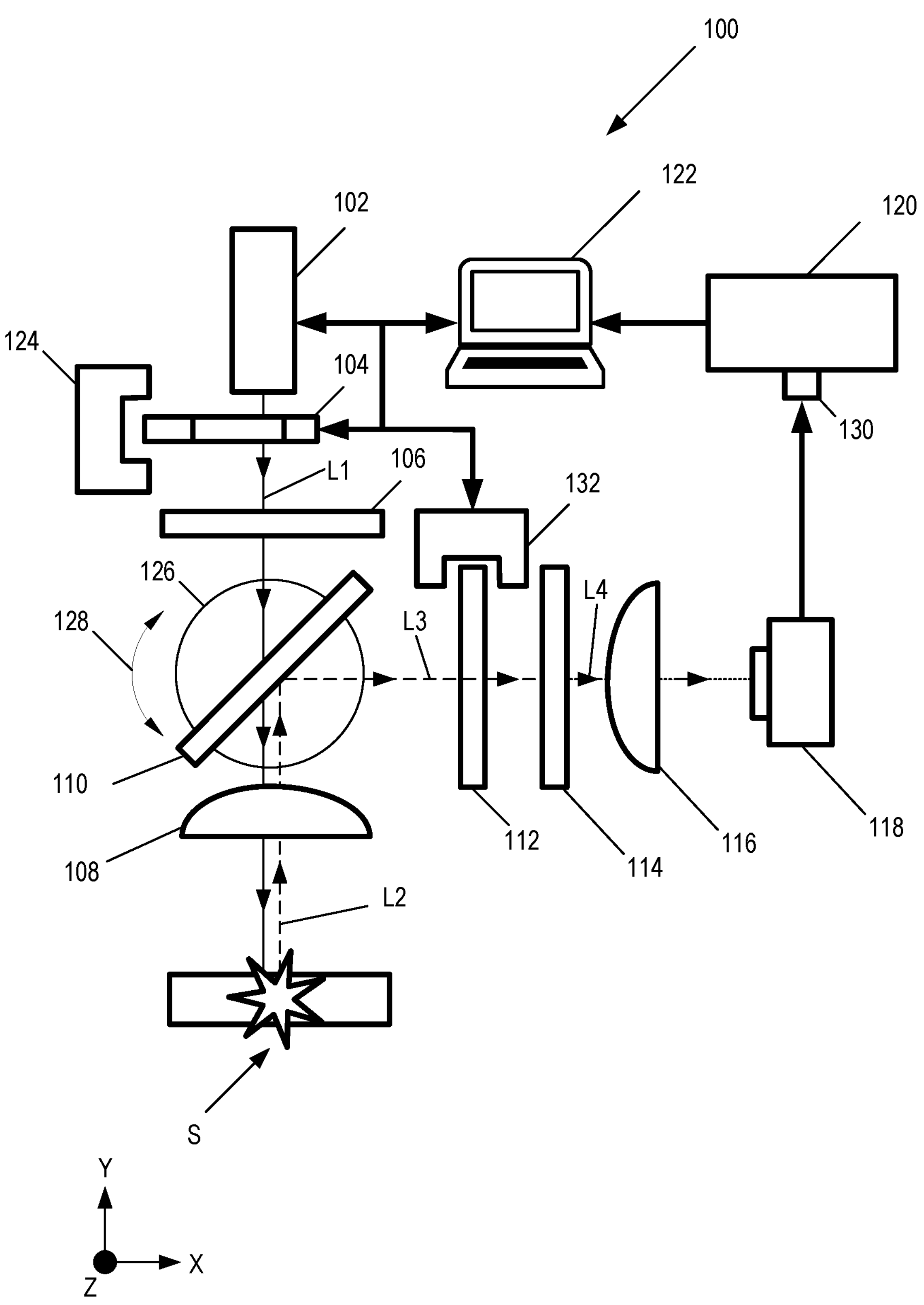
FIG. 1 illustrated a schematic functional diagram of an example dosimetry system, in accordance with the embodiments disclosed herein.

Various embodiments disclosed herein are described in detail with reference to the aforementioned figures. The drawings are provided for purposes of illustration only and merely depict example embodiments. These drawings are provided to facilitate the reader's understanding and shall not be considered limiting of the breadth, scope, or applicability of the embodiments. It should be noted that for clarity and ease of illustration these drawings are not necessarily made to scale.

DETAILED DESCRIPTION

The detailed description set forth below, in connection with the accompanying drawings, is intended as a description of various embodiments and is not intended to represent the only embodiments in which the disclosure may be practiced. The detailed description includes specific details for the purpose of providing a thorough understanding of the embodiments. However, it will be apparent that those skilled in the art will be able to understand the disclosure without these specific details. In some instances, well-known structures and components are shown in simplified form for brevity of description. Some of the surfaces have been left out or exaggerated for clarity and ease of explanation.

Reference throughout this disclosure to "embodiment" or "example" or "iteration" means that a particular feature, structure, or characteristic described in connection with the embodiment is included in at least one embodiment. Thus, appearances of the terms "embodiment" or "example" or "iteration" in various places throughout this specification are not necessarily all referring to the same embodiment. Furthermore, the particular features, structures, or characteristics may be combined in any suitable manner in one or more embodiments.

PDT involves three components: a photosensitizer, a light source, and tissue oxygen. The wavelength of the light source needs to be appropriate for exciting the photosensitizer to produce singlet oxygen, radicals, and/or reactive oxygen species. These are free radicals generated through electron abstraction or transfer from a substrate molecule and highly reactive state of oxygen known as singlet oxygen. The terms "radicals", "reactive oxygen species", and "oxygen radicals" as used herein will be understood to refer to radicals, reactive oxygen species, and/or combinations thereof that result from exciting the photosensitizers as disclosed herein. PDT is a multi-stage process. First a photosensitizer with minimal dark toxicity, in some embodiments, is administered to a target area (e.g., diseased tissue), either systemically or topically. When a sufficient amount of photosensitizer is applied to the target area, light is applied to the photosensitizer for a specified period, which activates the photosensitizer. Activating the photosensitizer produces radicals and/or reactive oxygen species (e.g. singlet oxygen), which elicit cell death of the diseased tissue. The light exposure supplies sufficient energy to stimulate the photosensitizer, but the dose period and energy levels are controlled so to not damage neighboring healthy tissue.

In various embodiments disclosed herein, the target area may be a part of the eye, such as a cornea of an eye. There is potential for Rose Bengal photodynamic antimicrobial therapy (RB-PDAT) as a therapy for treating infectious keratitis, keratoconus, as well as possibly OSSN, ocular surface cancers generally (for example, conjunctival proliferative vascular tumors), posterior capsule opacification, etc. RB-PDAT has been able to fully inhibit fungal and bacterial isolates derived from patients with infectious keratitis. RB-PDAT has been used on patients as an experimental therapy for corneal infection and approximately 72% of those patients avoided undergoing emergency corneal transplantation.

Riboflavin crosslinking (Riboflavin CXL), a similar procedure which uses riboflavin-5'-phosphate and ultraviolet A (UVA) light, may also have potential as a treatment for infectious keratitis. While the Riboflavin CXL procedure has been primarily focused on stiffening the cornea, the procedure may also demonstrate antimicrobial effects. For example, Riboflavin CXL is a key therapy for the treatment of keratoconus, and has also has shown potential for treating infectious keratitis.

Other photosensitizers have shown promise as well. For example, erythrosine-mediated photodynamic therapy (PDT) has been shown on *Candida albicans* to create a 1.97 $\log_{10}$ reduction in concentration. As another example, methylene blue-mediated PDT has been able to significantly reduce respiratory activity of keratitis derived *Acanthamoeba castellanii*, which also showed synergistic effects with traditional *Acanthamoeba* treatment regimens.

Finally, FDA approved photosensitizers Verteporfin, 5-aminolevulinic acid, and methyl aminolevulinate have been tested with a large number of cancers (skin, bladder, esophageal, breast, lung, gastrointestinal, prostate, ocular, and head and neck cancers), as well having use in treatment of age related macular degeneration, and several inflammatory and infectious diseases (psoriasis, acne vulgaris, sarcoidosis, verruca vulgaris, condyloma *acuminatum*, and cutaneous leishmaniasis).

The RB-PDAT treatment protocol may be based on the protocol of the FDA-approved Riboflavin CXL procedure. RB-PDAT works similarly, but has greater efficacy for the production of singlet oxygen ($^1O_2$). RB-PDAT works by treating the infected portion of the cornea with the photosensitive dye Rose Bengal (RB), and then exposing the cornea with light having wavelengths that correspond to (or are close to) excitation peaks of RB (e.g., within the absorption range of the photosensitizer), for example, 525 nm green light produced by an array of LEDs (Light Emitting Diode). Reactive $^1O_2$ is generated by the process and goes on to destroy the infecting microorganisms. An example of a PDT device is described in PCT/US2021/024683 filed on Mar. 29, 2021, the disclosure of which is incorporated herein by reference as if set forth in full. While preliminary results have been promising, a better understanding of the fundamental photochemical processes for generating $^1O_2$ may be required to optimize the treatment protocol. This optimization can maximize effectiveness of RB-PDAT and minimize side-effects. To make this possible, an accurate measure of dosage must be established.

Current standard dosage measurements for PDT rely on indirect measures such as fluence (J/cm$^2$) and/or irradiance (mW/cm$^2$) of light, concentration of the applied photosensitizer, and application time. However, these measures often do not accurately reflect the therapeutic effect, which is based on the amount of reactive oxygen (e.g., $^1O_2$) that is produced. This is because production of reactive oxygen requires adequate 1) light, 2) photosensitizer, and 3) free oxygen at the treatment area. Using only irradiance, fluence, and/or photosensitizer concentration as dosage measurements is limited because these values do not take into consideration factors such as free oxygen depletion, light absorption or scattering, and spatial distribution of the photosensitizer.

While some dosimeters for measuring $^1O_2$ may already exist, none have been specifically designed for the purpose of dosimetry of corneal PDT, and more specifically RB-PDAT. Similarly, for Riboflavin CXL, fluorescence or corneal stiffness based dosimeters have been produced, but none have been made to measure the generation of antimicrobial $^1O_2$. Existing dosimeters do not provide direct measurement of $^1O_2$ produced during PDT in the eye.

Embodiments disclosed herein provide for a cornea dosimeter (also referred to herein as a dosimetry system) designed for measuring generation of singlet oxygen produced from activation of a photosensitizer during PDT. Various embodiments disclosed herein measure singlet oxygen produced during RB-PDAT, Riboflavin CXL, and/or PDT using other photosensitizers having excitation ranges 250 to 900 nm. Embodiments herein provide for direct dosage measurement of singlet oxygen (e.g., $^1O_2$) produced by activation of photosensitizers. For example, embodiments herein provide for a dosimeter capable of measuring the luminescence output from the reactive oxygen produced by activating corresponding photosensitizers during RB-PDAT, Riboflavin CXL and other PDT utilizing photosensitizers having excitation ranges 250 to 900 nm. For example, embodiments herein are able to measure 1270 nm luminescence output from $^1O_2$. Various embodiments are also able to filter out background emissions (e.g., fluorescence from the activated photosensitizer and/or tissue autofluorescence). Using this direct form of dosimetry provides for improved accuracy of dosage measurement during RB-PDAT, Riboflavin CXL and other photosensitizers.

FIG. 1 illustrates a schematic functional diagram of dosimetry system or dosimeter 100, in accordance with the embodiments disclosed herein. FIG. 1 illustrates the dosimeter 100 as an optical system comprising a plurality of optical elements. Axes X, Y, and Z are provided in FIG. 1 as an illustrative reference only. Thus, while dosimeter 100 is depicted in the Y- and X-planes, it will be appreciated that the dosimeter 100 may be arranged on any desired plane, such that the optical components are capable to function as described herein. For example, the Y, X, and Z axis may be changed. Furthermore, additional optical elements not illustrated in FIG. 1 may be included as desired to meet structural constraints, for example, mirrors may be added to conform the dosimeter within a desired housing or structure.

Dosimeter 100 comprises a light source 102 configured to emit light that corresponds to (or is close to) an excitation peak of a photosensitizer applied sample S (e.g., within the absorption range of the photosensitizer). In some embodiments, sample S may be diseased tissue, such as a cornea of an eye. The light emitted from light source 102 activates the photosensitizer, which produces singlet oxygen ($^1O_2$) or reactive oxygen species. The $^1O_2$ produces a luminescence that is received by a photodetector 118 and, based on the received luminescence, a measurement of the produced $^1O_2$ can be obtained.

In the illustrative example shown in FIG. 1, the light source 102 emits light of the wavelength corresponding to the photosensitizer as a light beam L1. In various examples, the light source is a laser; however other light sources are possible such that the emitted light comprises the desired wavelength and exhibits coherence and collimation in a manner similar to that achieved by a laser light source (e.g., laser diodes and the like). For example, the light source 102 may be a lamp, light-emitting diodes (LEDs), or any light source desired. As another example, the light source 102 may comprise a plurality of light sources. For example, the light source 102 may comprise a laser and one or more lamps, LEDs, etc. The laser could be in an off state and one or more second light sources (external to the dosimeter system and/or part of the system) may be directed to the subject. The second light source could be angled with respect to the optical axis of the first light source (e.g., placed such that the optical axis is 45 degree off of the optical axis of the first light source).

The light source 102 may be controlled through the use of a shutter 104 that may be operated via controller 122 to block or allow light transmission. The light L1 may optionally be filtered to remove background noise and undesired wavelengths of light using, for example, an optical filter 106. The optical filter 106 may be transmissive to light of the desired wavelength peak (among other wavelengths) while blocking (e.g., absorbing or reflecting) other wavelengths. For example, the optical filter 106 may be an optical shortpass filter transparent in the 350 to 560 nm range, and up to 900 nm for longer wavelength excitation sources, while blocking wavelengths longer than the selected range (longer wavelength than near-infrared light for example). In another example, the optical filter 106 may be an optical bandpass filter having a center wavelength (CWL) within the selected range and a full width at half max (FWHM) selected to block wavelengths that are shorter and longer than the selected range (longer wavelength near-infrared light for example). That is, optical filter 106 may be selected to pass light in the visible spectrum light and, in some implementations, both visible spectrum light and near infrared spectrum light, while blocking longer near-infrared spectrum light. The light L1 is then focused onto the sample S by a first lens 108. More specifically, lens 108 focuses light L1 onto the area of the sample S on which the photosensitizer is applied.

The focused light L1 activates the photosensitizer, which produces $^1O_2$ or reactive oxygen species. The $^1O_2$ then produces luminescence at a wavelength, different from that of the excitation peak. Additionally, the photosensitizer may exhibit fluorescence having a corresponding wavelength that is based on the photosensitizer and/or the tissue may exhibit autofluorescence having corresponding wavelength. The fluorescence emitted by the photosensitizer, tissue autofluorescence, and any other source of light that is not the luminescence produced by the $^1O_2$ may be referred to herein as background noise and/or background signal.

The resulting emissions L2 (e.g., light emitted from sample S following incidence of the light L1) are collected by the first lens 108 (sometimes referred to herein as an objective lens), and directed to a dichroic mirror 110. The dichroic mirror 110 is selected to have a cutoff wavelength that reflects at least wavelengths corresponding to the luminescence of the $^1O_2$ and transmits other wavelengths. For example, the dichroic mirror 110 may be an optical shortpass dichroic mirror having a cutoff wavelength reflective to the wavelength of the luminescence and transmissive to shorter wavelengths. The cutoff wavelength may be between 900 and 1150 nm in various examples. The resulting reflected light L3 (e.g., short-wave infrared light) reflected by the dichroic mirror 110 toward an optical filter system 112. In the illustrated example, the dichroic mirror 110 reflects light L3 approximately 90 degrees from the optical axis of the light L2.

The optical filter system 112 may comprise one or more bandpass filters, one of which has a central wavelength (CWL) and a bandwidth (also referred to herein as a fullwidth at half max or FWHM) selected to transmit a desired wavelength band downstream, while blocking wavelengths outside the wavelength band. At least one of the bandpass filters may be selected to have CWL and FWHM to ensure the luminescence corresponding to the produced $^1O_2$ is transmitted downstream. The FWHM may be 60 nm or less, 50 nm or less, 40 nm or less, 20 nm or less, and 10 nm or less, as desired. In the illustrated example, the optical filter system 112 may have a CWL within a first predetermined range of the expected luminescence of the $^1O_2$. In some embodiments, the first predetermined range may have a lower end of the range at or above the cutoff wavelength of optical filter 114, and the upper end of the range may span up to the maximum wavelength that the photoreceiver 118 can measure. As an illustrative example, the lower end of the first predetermined range may be 100 nm from the expected peak luminescence, while the upper end may be 100 nm or up to the maximum wavelength that the photoreceiver can measure. Example CWLs may include, but are not limited to, 1160, 1200, 1210, 1230, 1250, 1270, 1277, 1280, 1290, 1300, and 1310 nm. The optical filter system 112 may serve to isolate and characterize the luminescence curve from the singlet oxygen from the background signal, such as, for example, the fluorescence from the photosensitizer and/or tissue autofluorescence. For example, the optical filter system 112 be a variable optical filter system comprising a plurality of filters that are switchable via switching member 132 (e.g., iteratively selected) in order to isolate the peak luminescence wavelength from background signals. The switching member 132 may be a sliding filter holder configured to permit the plurality of filters to be switch manually. In another example, the switching member 132 may be filter wheel operated under control of the controller 122 to automatically or semi-automatically switch between the plurality of filters. In various examples, the plurality of bandpass filters are a plurality of bandpass filters housed in the switching member 132, to measure the luminescence peak and neighboring background noise (e.g., FIG. 3). The CWL of the plurality of bandpass filters may each be within the first predetermined range of the expected luminescence of singlet oxygen, where each filter may be switched out with another to isolate the peak luminescence. In an illustrative example, four or more bandpass filters are included in the variable optical filter system.

To further remove the background signal, the light may be filtered by one or more optical filters 114. For example, the one or more optical filters 114 may be one or more optical longpass filters having cutoff wavelengths that are based on the optical filter system 112. The cutoff wavelength of the optical filters 114 may be below the lowest CWL of the optical filter system 112. In some implementations, the cutoff wavelength of the optical filter 114 may be separated from the lowest CWL of the optical filter system 112 by a wavelength gap. This wavelength gap may be beneficial dependent on the operating specifications of the optics of the dosimeter system (e.g., how steep the cutoff wavelength is for the optical filter 114, the FWHM of the optical filter system 112, etc.). For example, the optical filter 114 may be any one of a 1150 nm longpass filter, 1140 nm longpass filter, 1170 nm longpass filter, 1110 nm longpass filter, etc., as long as the cutoff wavelength is below the lowest CWL wavelength of the optical filter system 112. The resulting light L4 (e.g., luminescence of the $^1O_2$, filtered to substantially remove the background signal) is then collected by a second lens 116 and focused onto photoreceiver 118 (also referred to herein as a photodetector) sensitive to the wavelength of the luminescence. The photoreceiver 118 converts the received optical signal to an electrical output signal, for example, a voltage signal.

While the illustrative example of FIG. 1 shows the one or more optical filters 114 between the variable optical filter system 112 and the photoreceiver 118, the configuration is not so limited. For example, the one or more optical filters 114 may be positioned before the variable optical filter system 112, such that the variable optical filter system 112 is between the one or more optical filters 114 and the photoreceiver 118. As another example, where a plurality of optical filters 114 are utilized, one or more of the optical filters 114 may be positioned prior to the variable optical filter system 112, while another one or more optical filters1 114 may be between the variable optical filter system 112 and the photoreceiver 118.

The electrical output signal (sometimes referred to herein as a voltage signal) is then collected from the photoreceiver 118 through a wired or wireless connection to an electrical signal receiving device 120 configured to receive an electrical signal and output a voltage signal as a waveform representative of the received signal. Outputting may include a visual representations on a display of the variation of voltage over time and/or outputting to the controller 122. An example of the electrical signal receiving device 120 may be an oscilloscope or the like. The electrical signal receiving device data may be recorded onto the controller 122 and processed in memory, for example, through execution of computer program. The electrical signal receiving device 120 may be included as part of the controller 122 and/or as a separate device that is in wired or wireless communication with the controller 122. The controller 122 may be implemented as a computer system, for example, as computer system 400 of FIG. 4. Processed data provides a description of the amount of $^1O_2$ generated during activation of the photosensitizer applied to sample S, for example, as described in connection to FIGS. 2 and 3 below.

Removal of the background signal using one or more filters (e.g., filters 112 and/or 114) may be important to the calculation of generated $^1O_2$ quantity. This is because in the power range in which $^1O_2$ produces luminescence, there can be significant contribution to the light emitted from the sample S due to fluorescence from the photosensitizers, as well as from tissue autofluorescence. In some implementations, the background signal may also be measured, for example, by measuring the emitted light directly after sample S (e.g., before incidence on the dichroic mirror 110 and/or prior to the filters 112). In another implementation, background signals may be measured by measuring a detected signal when the light source is off, which measures ambient light and electronic/thermal noises. In some implementations, to separate out fluorescence of the photosensitizer and tissue autofluorescence from singlet oxygen luminescence, a singlet oxygen quencher (e.g., sodium azide, NaN3) may be used. With $NaN_3$, only background signals are be detected, and this could be subtracted from the total signal detected.

In some examples, the dosimeter may include one or more translation stages and/or rotation stages to facilitate alignment of the various optical elements. For example, first lens 108 and/or second lens 116 may be mounted on translation and/or rotational stages (not shown) such that their positions are adjustable to X, Y, or Z direction and rotatable to ensure proper alignment and focusing. Such translational mobility of the lens 108 and 116 may provide for adjustment of the focus of each respective lens and precise alignment. In some examples, the shutter 104 may be mounted on a translation stage 124 that allows for position adjustment in the X, Y, and/or Z direction. Additionally, the dichroic mirror 110 may be placed on a rotation stage 126 capable of rotation (as illustrated by the curved arrow 128) about an axis that is perpendicular to the optical axis of either L2 and/or L3 (e.g., about the Z axis in this example). In an example, the rotation stage is capable of rotating the dichroic mirror 110 by plus or minus 7 degrees, while the translations stages are capable of plus or minus 1.5 mm of movement in the X, Y, and/or Z direction. However, the magnitude of the rotational and translational movement is not limited to these examples and may be any magnitude and/or increment as desired for the particular application. As another example, at least the optical system of the dosimeter system 100 (e.g., from the light source to the photoreceiver 118) may be provided on a translation stage to provide for precise X, Y, Z, and rotational alignment of first lens 108 with the sample. In some implementations, both the electrical signal receiving device 120 and the controller 122 may also be provided on the translation stage of the optical system.

As an example, the photosensitizer applied to sample S may be RB (for RB-PDAT) having an excitation band of 500 to 560 nm, riboflavin-5'-phosphate (for riboflavin CXL) having an excitation band of 350 to 375 nm, or any other photosensitizer having an excitation range of 250 nm to 900 nm. Other example photosensitizers may include, but are not limited to, erythrosin B (e.g., for erythrosine-mediated photodynamic therapy), methylene blue (e.g., for methylene blue-mediated PDT), eosin Y, dihematoporphyrinether, hematoporphyrins derivatives including photofrin, Verteporfin, methyl aminolevulinate, 5-aminolevulinic acid, or any photosensitizer capable of producing $^1O_2$. In some embodiments, photosensitizers may be formulated as a liquid or film to be applied to target area. In another example, photosensitizers may be provided as a gel (e.g., similar to how riboflavin is currently provided by Avedro, Inc.). In another example, the photosensitizer could also be supplied intravenously.

An illustrative Rose Bengal formulation comprises 4 sterile strips of Rose Bengal (HUB Pharmaceuticals) immersed in a vial containing 5 cc of saline (0.9% NaCl) or BSS shaken vigorously for 1 minute generating a 0.1% RB solution and transferred to a syringe by aspiration and deposited on both sides of a clinically available sponge (e.g., 8 mm corneal sponge, Beaver Visitec International, Waltham, Massachusetts, USA). A sponge may be placed on the center of the corneal or scleral defect of an eye for treatment. The sponge soaked with the photosensitizer may be left on the cornea for 30 minutes while 2-3 drops of Rose Bengal (or other photosensitizer) solution are placed on the sponge at set time intervals (e.g., every 2 or 3 minutes). Should a 0.2% Rose Bengal solution be needed, only 2.5 cc of saline or BSS are placed in the vial.

Another example formulation is to add the appropriate weight of Rose Bengal in a dark brown glass vial sealed with a rubber septum which is autoclaved for sterility. Then 5 or 2.5 cc of the above described fluids may be added to generate a 0.1 or 0.2% Rose Bengal solution. The same or similar procedure can be used for riboflavin and any other photosensitizers that are available in powder form. In each case, a 0.2 μm filter may be used to aspirate the solution via a sterile syringe to prevent extraneous matter from contaminating the solution.

In an illustrative example, the light source 102 is a laser configured to emit light having a wavelength that corresponds to the Rose Bengal excitation band of 500 to 560 nm (for RB-PDAT), a wavelength that corresponds to the riboflavin-5'-phosphate excitation band of 350 to 375 nm (for riboflavin CXL), or a matching excitation range for a given photosensitizer. In some implementations, the laser may emit light having an optical power of between approximately 1 mW and approximately 50 mW; however, the laser may emit any desired power as desired for the designed application. As described above, the laser $^1O_2$ may be controlled through the use of shutter 104 to block or allow laser transmission. The laser light L1 may be filtered to remove IR emission using a KG3 glass filter or other optical shortpass filter, for example, transparent from 350 to 560 nm (up to 900 nm for longer wavelength excitation lasers) as an illustrative example of optical filter 106. To control laser power, an additional neutral density filter may also be placed in the optical path of the laser to attenuate the laser. In this example, the first lens 108 may be a 20× objective lens having a focal length of 9 mm. However, other objective lens configurations may be applicable as desired for the physical constraints of the dosimeter 100.

The light L1 activates the photosensitizer, which generates $^1O_2$ that produce luminescence. $^1O_2$ produces luminescence at a peak wavelength of approximately 1270 nm plus or minus 10 nm, with a FWHM of approximately 25 to 35 nm. Additionally, the irradiated sample may produce a background signal (e.g., fluorescence from the photosensitizer and/or the tissue autofluorescence) that is emitted with the luminescence as light L2.

Light L2 emitted from the sample S is collected by the same lens 108, and reflected using a shortpass dichroic mirror with a cutoff between 900 and 1150 nm as an example of the dichroic mirror 110. The reflected short-wave infrared light L3 is then filtered through each of a plurality of bandpass filters separately, having a CWL within the first predetermined range of the expected luminescence of $^1O_2$ (e.g., an example of optical filter system 112). For example, three or more or four or more bandpass filters may be utilized in a variable optical filter system, each having a CWL within the first predetermined range of the expected luminescence of $^1O_2$. Since $^1O_2$ produces luminescence at approximately 1270 nm, a 1277 nm bandpass filter may be used to isolate the for $^1O_2$ signal, and other CWLs (e.g., 1200 nm, 1250 nm, 1300 nm, etc.) may be used to select background signals that can be used to differentiate the $^1O_2$ luminescence peak near 1277 nm. By performing the measurements using each bandpass filter separately, the luminescence curve from $^1O_2$ can be isolated and characterized by the dosimeter 100 (e.g., as described in greater detail in connection with FIG. 3). While example CWLs of 1200 nm, 1250 nm, 1277 nm, and 1300 nm are used herein, embodiments herein are not so limited and any CWL may be used such that the CWL is within the first predetermined range of the wavelength of the luminescence produced by $^1O_2$ (e.g., bandpass filter CWL of 1140, 1170, 1210, 1230, 1250, 1270, 1280, 1290, 1310 nm, etc.).

To further remove the background signal, the light is then filtered by one or more optical longpass filters (e.g., as examples of the one or more optical filters 114). The one or more longpass filters may comprise cutoff wavelengths at or below the lowest cutoff wavelength of the optical filter system 112. In the illustrative example, the optical longpass filter may have a 1150 nm cutoff wavelength; however, other cutoff wavelengths are possible (e.g., 1140 nm longpass filter, 1170 nm longpass filter, 1110 nm longpass filter, etc.). In some embodiments, two or more optical longpass filters may be utilized, each having the same or different cutoff wavelengths.

The remaining, filtered light is then collected by a focusing lens (e.g., an example of the second lens 116), which has a focal length of 8 mm in this example. The focusing lens 116 focuses the light L4 onto a photoreceiver 118, for example, an InGaAs photoreceiver sensitive in the femtowatt range from 800-1700 nm.

Measurement of background signal using multiple filters may improve calculations as to what part of the signal is not from $^1O_2$. This is because in the femtowatt range, there can be significant contribution to the signal due to fluorescence from the Rose Bengal or riboflavin-5'-phosphate dye, as well as from tissue autofluorescence.

A voltage signal may be collected from the photoreceiver 118 through a Bayonet Neill-Concelman (BNC) cable (or any quick connect/disconnect radio frequency connector), to a BNC terminator 130 set to, for example, 10 kΩ, and then to electrical signal receiving device 120. A BNC terminator may prevent RF signals from being reflected back from the end of an electronic line that would otherwise cause interference and noise. Finally, the electrical signal receiving device data is recorded onto the computer 122.

By processing the measurement data, a description of the amount of $^1O_2$ generated during RB-PDAT or Riboflavin CXL application can be determined. For example, voltages in the voltage signal output from the electrical signal receiving device 120 may correspond to a number of $^1O_2$ molecules.

Figure 2:
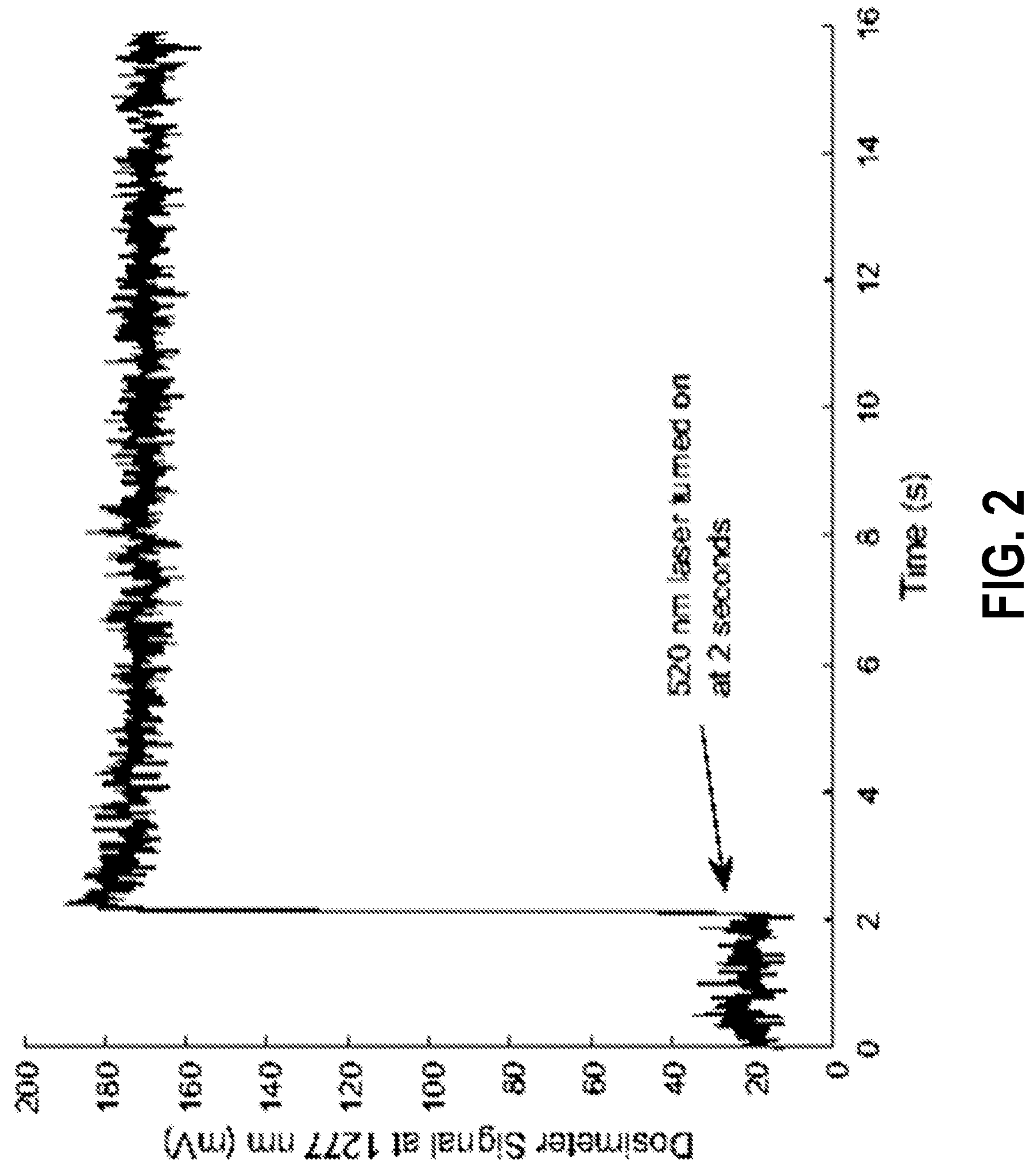
FIG. 2 is a graph depicting an example dosage measurement using the dosimetry system of FIG. 1.

FIG. 2 is a graph depicting an example dosage measurement using the dosimeter according to the embodiments disclosed herein. FIG. 2 illustrates how the amount of $^1O_2$ generated during an example RB-PDAT application may be determined based on measurement data acquired by embodiments disclosed herein (e.g., dosimeter 100). While FIG. 2 is generated based on performing RB-PDAT, it will be appreciated that PDT using the other photosensitizers disclosed herein (e.g., Riboflavin CXL and the like) can be applied and similar results generated.

FIG. 2 depicts a raw signal in mV on the Y vertical axis as a function of time in seconds(s) as measured by an example implementation of the dosimeter 100. The signal in m V may be an example voltage signal from the photoreceiver 118 of FIG. 1 as a function of time. The graph of FIG. 2 may be generated at the controller 122 and presented via a display. In this example, a 0.1% RB treated donor cornea (e.g., sample S of FIG. 1) is irradiated with a 520 nm green laser (e.g., light source 102 of FIG. 1) and focused on to the target area by a 20× objective lens having a working distance (WD) of 3.2 mm (e.g., first lens 108 of FIG. 1). The light emitted from the sample S as light L2 is filtered through 1277 nm CWL bandpass filter (e.g., optical filter system 112 of FIG. 1) and is collected by the photoreceiver 118. As depicted in FIG. 2, the laser is turned on at the 2 second mark resulting in a noticeable increase in collected power of 1277 nm light L4 as produced by $^1O_2$ generated by activation of the RB applied to the donor cornea. For this example, one volt of the voltage signal at the photoreceiver 118 corresponds to $1.36\times10^{10}$ of generated $^1O_2$ molecules. This may be calculated based on collection angles of lens 108, the luminescence lifetime of $^1O_2$, the transmission of the optical system, luminescence wavelength, and the InGaAs photoreceiver properties (responsivity at given wavelength, gain).

As an example, the number singlet oxygen molecules produced per second in the measured volume, $n_{1O_2}(t)$, is proportional to measured luminescence signal $L_{measured}(t)$ (photons $s^{-1}$ @ 1277 nm) as shown below:

$$n_{1O_2}(t) = \frac{\tau_L * L_{measured}(t)}{f_{collected}} \quad \text{Eq. (1)}$$

where $\tau_L = k_L^{-1}$ is the luminescence lifetime ($\tau_L$=5.55 s for $^1O_2$ in water) and $f_{collected}$ is the fraction of generated photons that are collected by the system. While TL was determined in water, it does not change with differing media.

Calculation of $f_{collected}$ is based on product of the transmission and numerical aperture of the optical system at 1277 nm. In this example, total transmission of the optics at 1277 nm is approximately 69%, and the numerical aperture (NA) of lens 108 (e.g. 0.4 for this example). The fraction of the total luminescence output collected by lens 108 is calculated by dividing the solid angle collected by lens 108 (a function of NA) by the solid angle of the sphere of isotropic $^1O_2$ luminescence (4×). For the illustrative example described in connection to FIG. 1, $f_{collected}$ is approximately $2.9\times10^{-2}$. The conversion from signal to $^1O_2$ dose assumes that the value of the collection efficiency is constant across experiments. In the illustrative example, a microscope objective with high numerical aperture (NA=0.4) was used to collect the signal. Due to the high numerical aperture, the system will be more sensitive to axial positioning errors, which may produce variations in the collection efficiency. In clinical use, a significantly lower numerical aperture providing a significantly longer depth of focus could be implemented to meet the requirement for a longer working distance. The clinical system would therefore be less sensitive to variations in position and provide a more reliable conversion factor. Finally, $L_{measured}$ (t) can be calculated based on the characteristics of the photoreceiver 118 (for example, a InGaAs photoreceiver):

$$L_{measured}(t) = \frac{V_{OUT}}{R(\lambda) * G * h\nu} \quad \text{Eq. (2)}$$

where $L_{measured}(t)$ is optical power incident on the photoreceiver (photons $s^{-1}$), $V_{OUT}$ is the measured output voltage (V), $R(\lambda)$ is responsivity of the photoreceiver at a given wavelength (approximately 0.9 A/W @ 1277 nm), G is detector gain ($10^{11}$ V/A±10%) and hv is the photon energy at 1277 nm ($1.56\times10^{-19}$ J). With these parameters and combining Eq. (1) and (2) to get:

$$n_{1O_2}(t) = 1.36\times10^{10} * V_{OUT} \quad \text{Eq. (3)}$$

From Equation (3) the instantaneous number of $^1O_2$ molecules present in the measured volume can be calculated based on the dosimeter voltage signal, as well as properties of the photoreceiver 118 and system optics. The value in Eq. (3) could be converted to μM by dividing $n_{1O_2}(t)$ by the relevant phantom volume (i.e. volume over which $^1O_2$ luminescence reaches the detector 118).

To determine the cumulative $^1O_2$ dose, $^1O_{2,dose}$, Eq. (3) can be integrated over the length of the collection period, t:

$$1_{O_{2,dose}} \equiv \frac{1}{\tau_D}\int_0^t n_{1_{O_2}}(t)dt \quad \text{Eq. (4)}$$

$\tau_D$ is measured $^1O_2$ lifetime within a given media. For tissue, $\tau_D$≈30-180 ns, for pure $H_2O$ $\tau_D$≈4 µs, pure $D_2O$ $\tau_D$≈68.1 µs and for 200 mM $NaN_3$ in $H_2O$, $\tau_D$ is calculated ≈185 ns Measurement of $^1O_2$ dosage can improve RB-PDAT or Riboflavin CXL because dosage measurements would give precise dosage information about the therapy. This information could be used, for example, to correlate findings of therapeutic efficacy to hone in on what the ideal doses are for a given disease/treatment.

For example: there are millions of combinations one could choose from for photosensitizer, photosensitizer concentration, photosensitizer solvent (saline, vs. water, vs. BSS, vs. something else), photosensitizer treatment time, excitation light wavelength, light source, fluence rate, total energy (i.e. how long did you apply the light for and at what strength/fluence rate), light is pulsed, at what rate, whether supplemental oxygen is added, whether adjuvants are added to the photosensitizer solution, etc. In addition, different photosensitizers have different distribution within the cornea.

Instead of trying every combination in vitro, in vivo, or clinically with the microbes/cancer/disease model to be treated, predictions can be made using these embodiments of the dosimeter systems disclosed herein. For example, to test if a particular MRSA keratitis strain is treated in patients better with photosensitizer A, B, C, or D, embodiments disclosed herein may be used with equivalent treatment protocols but changing the photosensitizer between each arm to see how much $^1O_2$ is produced on the cornea. With that information, it is possible to estimate of how much $^1O_2$ the *S. aureus* is exposed to during the therapy on the corneal surface. Photosensitizers can be selected to conduct further studies based on that information. Similarly, adding supplemental oxygen to the corneal surface can be tested to see if it makes a difference to singlet oxygen production. If $^1O_2$ production increases according to dosimeter measurements, then the addition of supplemental oxygen can be tested with the disease model. Furthermore, evaluation can be made to see if changing the photosensitizer solvent causes there to be a difference to singlet oxygen production. In addition, the effects of different photosensitizer concentration on singlet oxygen production may be examined. Higher photosensitizer concentration may lead to toxicity, but lower concentration may produce insufficient singlet oxygen for an effective therapy. Adjusting the fluence rate or total energy can also change $^1O_2$ production, and the dosimeter can provide information on the size of these changes in $^1O_2$. With these data, a therapeutic window for $^1O_2$ dosage can be established for each disease. The treatment parameters can be subsequently modified such that the output $^1O_2$ falls within the therapeutic window. Embodiments herein can provide information how much these variables plays a role.

As another example, oxygen depletion may play a role during RB-PDAT and Riboflavin CXL and this effect can be observed in real time with usage of the embodiments disclosed herein. Similarly, modifications of light pulses may be made to see whether $^1O_2$ is replenished after a certain window of having the excitation light turned off or modulated. Thus, as described above, embodiments herein are able to maximize $^1O_2$ production by determining the window during which oxygen replenish the tissue.

Figure 3:
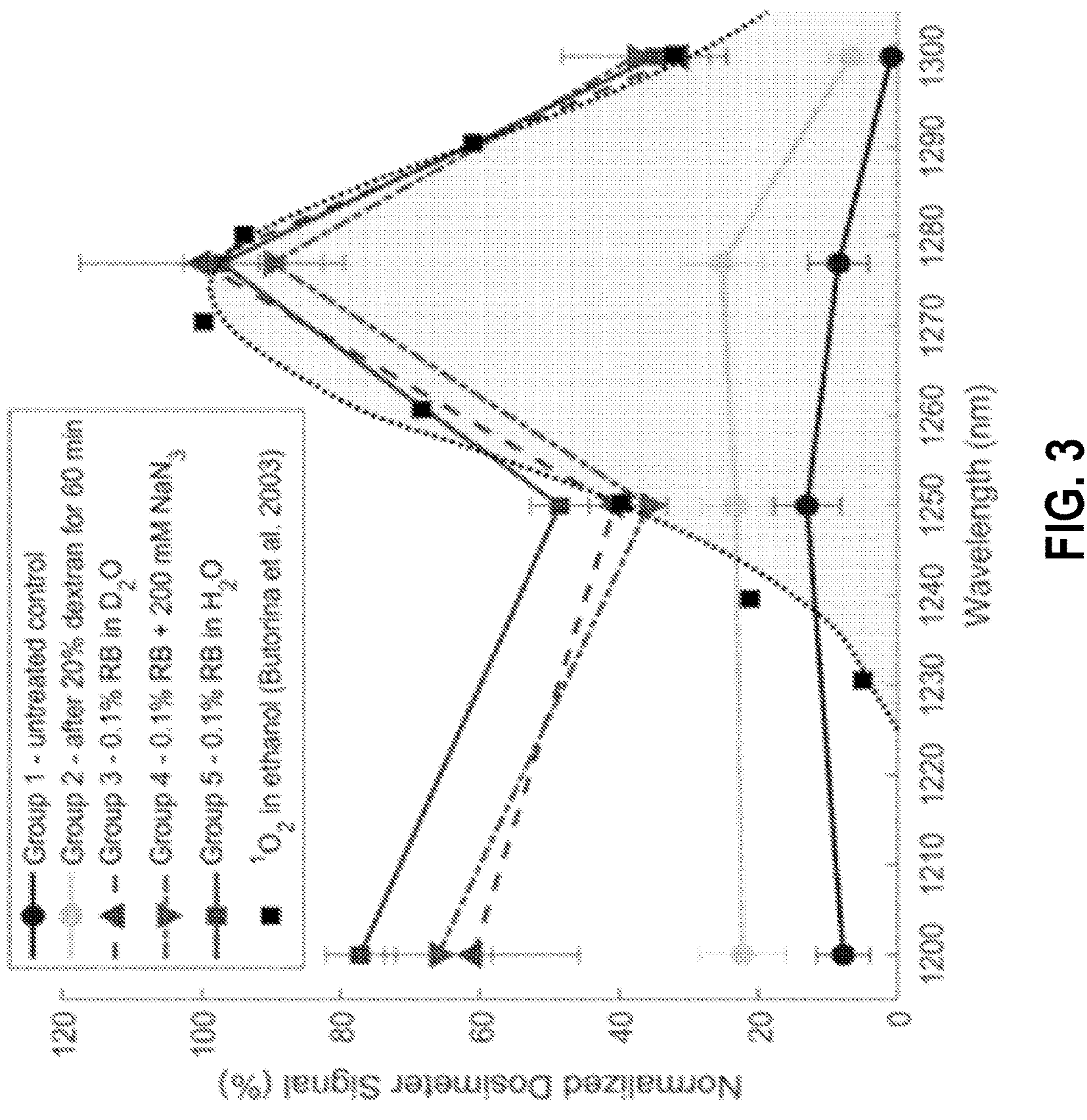
FIG. 3 is another graph depicting an example measurement signal peak isolation using the dosimetry system of FIG. 1.

FIG. 3 is another graph depicting an example dosage measurement using the dosimeter according to the embodiments disclosed herein. FIG. 3 depicts a signal, on the vertical axis, received from the dosimeter 100 (e.g., detected at the photoreceiver 118) that has been normalized and plotted as a function of wavelength on the horizontal axis.

The signals were detected from five donor eye groups from the same experimental setup (e.g., the same dosimeter 100). Signals were detected from human donor eyes from same experiment (n=3 per group, except group 2 where n=7) and normalized. The signals were filtered separately through a 1200, 1250, 1277, or 1300 nm bandpass filters (e.g., variable optical filter system 112) and measured three times per filter. Before Rose Bengal (RB) treatment, three eyes were measured with the dosimeter system disclosed herein (Group 1). The eyes were then treated with 20% dextran in $H_2O$ for 60 minutes to dehydrate corneas to physiologic thickness and measured with the dosimeter system disclosed herein (Group 2). The eyes were then treated with 0.1% RB in $D_2O$, a $^1O_2$ signal booster, (Group 3), in 200 mM sodium azide (e.g., NaN3 function as a $^1O_2$ quencher for Group 4), or in $H_2O$ (Group 5).

The light produced by each donor eye was filtered through 1200, 1250, 1277, and 1300 nm bandpass filters (e.g., at optical filter system 112) and measured by the photoreceiver 118 three times per filter. That is, with reference to FIG. 1, for example, light L3 was filtered separately by a 1200 nm bandpass filter, a 1250 nm bandpass, a 1277 nm bandpass filter, and a 1300 nm bandpass filter. The measurements for each filter were performed three times providing a standard deviation at each filter measurement as illustrated in FIG. 3. FIG. 3 illustrates a signal peak measured between 1250 nm and 1300 nm (e.g., at the 1277 nm bandpass filter). This peak corresponds to the expected luminescence that would be generated by $^1O_2$, for example, a known reference signal for $^1O_2$ that has been generated in ethanol. Thus, FIG. 3 illustrates the ability of the dosimeter 100 to detect $^1O_2$ generation based on detecting a signal peak at the expected wavelength of luminescence produced by $^1O_2$ due to activation of RB as a photosensitizer.

Figure 4:
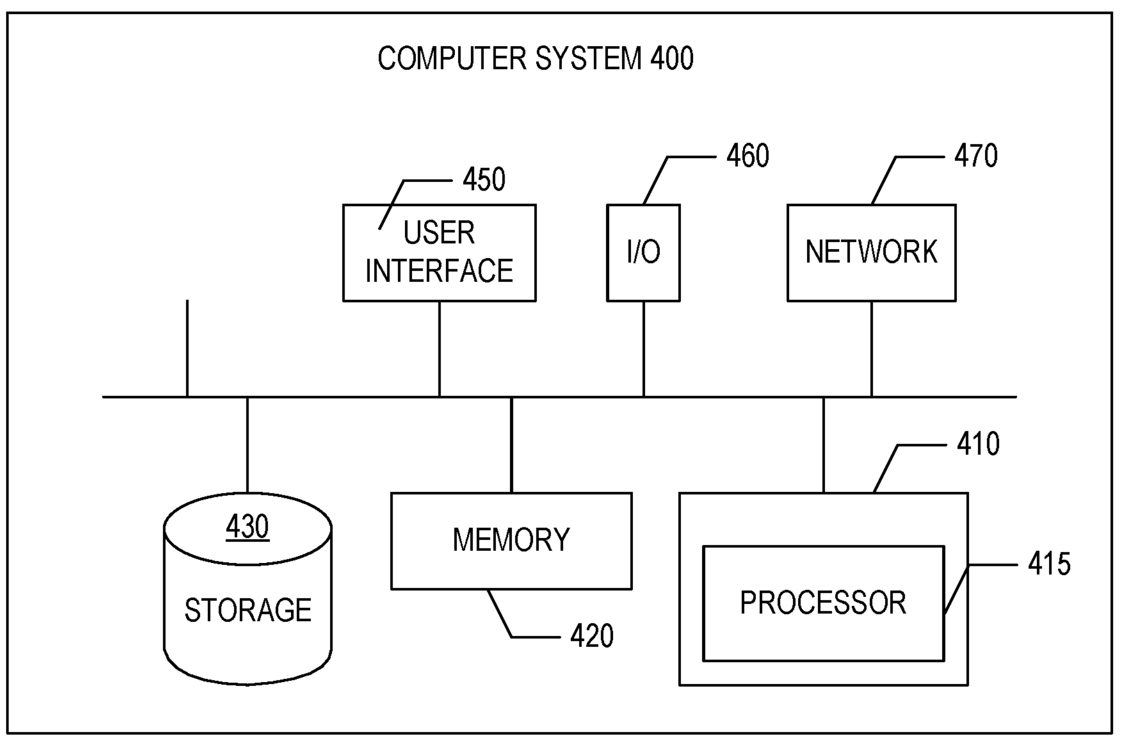
FIG. 4 is a schematic block diagram illustrating an example wired or wireless computer system according to embodiments of the present disclosure.

FIG. 4 is a functional block diagram of one embodiment of an exemplary controller in the form of a computer system 400 which can be used as part of the various embodiments described here. The computer system 400 may be implemented as the controller 122 of FIG. 1 in various embodiments. The computer system 400 includes a controller 410 having one or more processors 415, a memory 420, storage 430, a user interface 450, an input/output (I/O) interface 460, and a network interface 470. These components are interconnected by a common bus 480. Alternatively, different connection configurations can be used, such as a star pattern with the controller at the center.

The controller 410 is a programmable processor and controls the operation of the computer system 400 and its components. The controller 410 loads instructions from the memory 420 or an embedded controller memory (not shown) and executes these instructions to control the system as described above. These instructions may cause the controller 410 to perform the functions described throughout this disclosure, for example, in connection to FIGS. 1-3.

Memory 420 stores data temporarily for use by the components of the computer system 400. In one embodiment, memory 420 is implemented as RAM. In one embodiment, memory 420 also includes long-term or permanent memory, such as flash memory and/or ROM.

Storage 430 stores data temporarily or long term for use by the components of the computer system 400. In one embodiment, storage 430 is a hard disk drive. Storage 430 stores information for use by the one or more processors 415. Storage 430 also stores data generated by one or more processors 415.

The user interface 450 includes components for accepting user input from a user of the computer system 400 and presenting information to the user. In one embodiment, the user interface 450 includes a keyboard, a mouse, audio speakers, and a display. The controller 410 uses input from the user to adjust the operation of the computer system 400. The user interface 450 may be an example of user interface included as part of or coupled to controller 122 of FIG. 1.

The I/O interface 460 includes one or more I/O ports to connect to corresponding I/O devices, such as the laser source(s) and the robotic arm referenced above. In various embodiments, the ports of the I/O interface 460 include ports such as: USB ports, PCMCIA ports, serial ports, and/or parallel ports. In another embodiment, the I/O interface 460 includes a wireless interface for communication with external devices wirelessly.

A network interface 470 can be included as a wired and/or wireless network connection, such as an RJ-45 or "Wi-Fi" interface (802.11) supporting, for example, an Ethernet connection.

The computer system 400 includes additional hardware and software typical of computer systems (e.g., power, cooling, operating system), though these components are not specifically shown in FIG. 4 for simplicity. In other embodiments, different configurations of the computer system can be used (e.g., different bus or storage configurations or a multi-processor configuration).

Those of skill in the art will appreciate that the various illustrative logical blocks, modules, circuits, and steps described in connection with the above described figures and the embodiments disclosed herein can often be implemented as electronic hardware, computer software, or combinations of both. To clearly illustrate the interchangeability of hardware and software, various illustrative components, blocks, modules, circuits, and steps are described herein generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a component, block, module, circuit, or step is for ease of description. Specific functions or steps can be moved from one component, block, module, circuit, or step to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Combinations, described herein, such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, and any such combination may contain one or more members of its constituents A, B, and/or C. For example, a combination of A and B may comprise one A and multiple B's, multiple A's and one B, or multiple A's and multiple B's.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A dosimeter for photodynamic therapy, the dosimeter comprising:

a variable optical filter system configured to:

receive a second light, the second light comprising luminescence produced by singlet oxygen and one or more background signals, each of which are based on irradiating a sample with a first light comprising a first wavelength within an excitation range of a photosensitizer applied to the sample, wherein activating the photosensitizer produces the singlet oxygen, and selectively transmit the luminescence and the one or more background signals as a third light, the variable optical filter system comprising a plurality of optical bandpass filters that are switchable to selectively transmit the luminescence and the one or more background signals;

a photoreceiver configured to receive the third light and configured to generate electrical output signals corresponding to the luminescence and the one or more background signals, the electrical output signals being indicative of an amount of the singlet oxygen produced based on activating the photosensitizer; and a controller communicatively coupled to the photoreceiver and configured to receive the electrical output signals and determine a number of molecules of the singlet oxygen, produced by activating the photosensitizer with the first light, based on the electrical output signals.

2. The dosimeter of claim 1, wherein the excitation range includes an excitation peak of the photosensitizer that is between 250 to 900 nm.

3. The dosimeter of claim 1, wherein the photosensitizer is selected from a group consisting of Rose Bengal, Erythrosin B, Eosin Y, riboflavin, methylene blue, dihematoporphyrinether, hematoporphyrins derivatives, Verteporfin, 5-aminolevulinic acid, and methyl aminolevulinate.

4. The dosimeter of claim 2, wherein the singlet oxygen is $^1O_2$ and the luminescence has a wavelength of between approximately 1260 nm and approximately 1280 nm.

5. The dosimeter of claim 1, wherein each of the plurality of optical bandpass filters comprises a central wavelength (CWL) within a predetermined range of a second wavelength that represents an expected luminescence of the singlet oxygen.

6. The dosimeter of claim 5, wherein an upper end of the predetermined range is based on a maximum detectable wavelength of the photosensitizer.

7. The dosimeter of claim 1, wherein the plurality of optical bandpass filters comprises at least three optical bandpass filters.

8. The dosimeter of claim 1, further comprising a first lens configured to focus the first light onto the sample and collect the second light emitted from the sample.

9. The dosimeter of claim 8, further comprising an optical shortpass filter configured to receive the first light and transmit filtered light to the sample, the optical shortpass filter configured to block infrared spectrum light.

10. The dosimeter of claim 9, further comprising a dichroic mirror positioned between the sample and the variable optical filter system and configured to receive the second light from the sample and direct reflected light to the variable optical filter system, the dichroic mirror comprising a cutoff wavelength selected to reflect light of at least a second wavelength that represents an expected luminescence of the singlet oxygen.

11. The dosimeter of claim 1, further comprising one or more optical longpass filters, the one or more optical longpass filters are (i) positioned between the variable optical filter system and the photoreceiver or (ii) positioned such that the variable optical filter system is between the one or more longpass filters and the photoreceiver, the one or more optical longpass filters having cutoff wavelengths based on the plurality of optical bandpass filters.

12. The dosimeter of claim 11, wherein the one or more optical longpass filters comprises at least two optical longpass filters.

13. The dosimeter of claim 11, wherein the cutoff wavelengths of the one or more optical longpass filters are at or below a lowest central wavelength of the plurality of optical bandpass filters.

14. The dosimeter of claim 1, wherein the photoreceiver is an InGaAs photoreceiver.

15. The dosimeter of claim 1, further comprising a light source configured to emit the first light so to irradiate the sample comprising the photosensitizer applied thereto.

16. The dosimeter of claim 15, wherein the light source emits the first light at a wavelength between 250 nm to 900 nm, or wavelength that corresponds to the excitation band of the selected photosensitizer.

17. The dosimeter of claim 1, wherein the number of molecules of the singlet oxygen are determined based on:

$$n(t) = \frac{\tau_L * L_{measured}(t)}{f_{collected}}$$

wherein n(t) is the number of molecules at a time t, $\tau_L$ is a luminescence lifetime, $L_{measured}(t)$ is a measured luminescence signal from the electrical output signals at the time t, and $f_{collected}$ is a fraction of generated photons that is collected by the photoreceiver.

18. A dosimetry system comprising:

a variable optical filter system configured to:

receive a second light, the second light comprising luminescence produced by singlet oxygen and one or more background signals, each of which are based on irradiating a sample with a first light comprising a first wavelength within an excitation range of a photosensitizer applied to the sample, wherein activating the photosensitizer produces the singlet oxygen, and selectively transmit the luminescence and the one or more background signals as a third light, the variable optical filter system comprising a plurality of optical bandpass filters that are switchable to selectively transmit the luminescence and the one or more background signals;

a photoreceiver configured to receive the third light and configured to generate electrical output signals corresponding to the luminescence and the one or more background signals, the electrical output signals being indicative of an amount of the singlet oxygen produced based on activating the photosensitizer; and a controller communicatively coupled to the photoreceiver and configured to receive the electrical output signals from the photoreceiver, determine a number of molecules of the singlet oxygen, produced by activating the photosensitizer with the first light, based on the electrical output signals, and generate a dosage measurement based on the determined number of molecules of the singlet oxygen.

19. The dosimetry system of claim 18, further comprising an electrical signal receiving device communicatively coupled to the photoreceiver and configured to receive the electrical output signals from the photoreceiver and communicate the received electrical output signals to the controller.

20. A method for measuring dosage for photodynamic therapy treatment, the method comprising:

deploying a dosimeter system according to claim 1;

iteratively selecting each optical bandpass filter of the plurality of optical bandpass filters to selectively filter the second light;

for each optical bandpass filter, measuring, by the photoreceiver, an optical signal of the filtered second light and outputting the electrical output signal corresponding to the respective optical bandpass filter to the controller; and by the controller, determining the number of molecules of the singlet oxygen, produced by activating the photosensitizer with the first light, based on the electrical output signals.

21. The method of claim 20, wherein the singlet oxygen is $^1O_2$ and the electrical output signal is a voltage signal, wherein voltages in the voltage signal correspond to the number of $^1O_2$ molecules.

* * * * *